(12) United States Patent
Alam

(10) Patent No.: US 7,244,828 B2
(45) Date of Patent: *Jul. 17, 2007

(54) AGENT FOR PROTEIN PRECIPITATION, A METHOD OF PROTEIN PRECIPITATION, A METHOD OF PROTEIN ASSAY USING PROTEIN PRECIPITATION AGENT, AND A KIT FOR PROTEIN ASSAY

(76) Inventor: Aftab Alam, Geno Technology, Inc., 3047 Barfold Ave., St. Louis, MO (US) 63143

( * ) Notice: Subject to any disclaimer, the term of this patent is extended or adjusted under 35 U.S.C. 154(b) by 89 days.

This patent is subject to a terminal disclaimer.

(21) Appl. No.: 11/048,892

(22) Filed: Feb. 3, 2005

(65) Prior Publication Data

US 2005/0170519 A1   Aug. 4, 2005

Related U.S. Application Data

(60) Continuation of application No. 09/842,838, filed on Apr. 27, 2001, now Pat. No. 6,875,617, which is a continuation-in-part of application No. 09/223,738, filed on Dec. 31, 1998, now abandoned, which is a division of application No. 08/965,873, filed on Nov. 7, 1997, now Pat. No. 5,900,376, and a division of application No. 09/507,977, filed on Feb. 22, 2000, now abandoned, which is a continuation-in-part of application No. 09/249,499, filed on Feb. 12, 1999, now abandoned, which is a continuation-in-part of application No. 08/965,873, filed on Nov. 7, 1997, now Pat. No. 5,900,376.

(51) Int. Cl.
*A23J 1/00* (2006.01)
*G01N 33/00* (2006.01)

(52) U.S. Cl. ............... 530/419; 530/418; 530/420; 530/427; 436/86; 436/166; 436/177

(58) Field of Classification Search ............... 530/419, 530/418, 420, 427; 436/86, 166, 177
See application file for complete search history.

(56) References Cited

U.S. PATENT DOCUMENTS 4,801,690 A   1/1989   Brinton, Jr. et al.
5,089,602 A   2/1992   Isliker et al.
5,231,034 A   7/1993   Fleming
5,300,440 A   4/1994   Alam
5,900,376 A   5/1999   Das et al.
6,875,617 B2 * 4/2005   Alam ........................ 436/86

OTHER PUBLICATIONS

Carraro et al., Electrophoresis, 1991, 12, p. 1005-1010.
Carraro et al., Biochem & Biophys. Res. Commun., 1994, 200, p. 916-924 [AM].
Sandri, et al., Anal. Biochem., 1993, 213, p. 34-39.
Wang et al., BioTech., 1996, 20, p. 662-668.
Bensadoun & Weinstein, Anayl Biochem., 1976, 70, p. 241-250.
"A simplification of the Protein Assay Method of Lowry et al. Which is More Generally Applicable"; Gary L. Peterson; Analytical Biochemistry 83, 346-356 (1977).
"Assay of Proteins in the Presence of Interfering Materials" Andre Bensadoun et al.; Analytical Biochemistry 70, 241-250 (1976).
"Protein Measurement Using Bicinchoninic Acid: Elimination of Interfering Substances"; Rhoderick E. Brown et al.; Analytical Biochemistry 180, 136-139 (1989).
"Acid Precipitation of Protein in the Presence of Triton X-100 and Deoxycholate"; Retz et al. Analytical Biochemistry 79, 457-461 (1977).
"Efficient Precipitation and Accurate Quantitation of Detergent-Solubilized Membrane Proteins", Chang; Analytical Biochemistry 205, 22-26 (1992).
"A Simple Procedure for Protein Determination by the Lowry Method in Dilute Solutions and in the Presence of Interfering Substances", Polacheck et al., Analytical Biochemistry 117, 311-314 (1981).
BIO-RAD Catalog of 1993, Life Science Research Products, pp. 71-74.
Bensadoun et al., Analytical Biochemistry, vol. 70, pp. 241-250, 1976.
Carraro et al., Biochem. & Biophys. Res. Commun., vol. 200 pp. 916-924, 1994.

* cited by examiner

*Primary Examiner*—Jon Weber
*Assistant Examiner*—Abdel A. Mohamed
(74) *Attorney, Agent, or Firm*—Arent Fox LLP

(57) ABSTRACT

A method of protein precipitation, concentration and removal of non-protein agents from the protein solution wherein the protein solution is treated with a protein-precipitation agent containing an acidic agent, a salt and a precipitate forming agent. After precipitation, the protein precipitate is washed with a water miscible organic solvent agent to remove non-protein agents present in the protein precipitate.

23 Claims, 9 Drawing Sheets

Left                                    Right

AGENT FOR PROTEIN PRECIPITATION, A METHOD OF PROTEIN PRECIPITATION, A METHOD OF PROTEIN ASSAY USING PROTEIN PRECIPITATION AGENT, AND A KIT FOR PROTEIN ASSAY

CROSS-REFERENCE TO RELATED APPLICATION

This is a Continuation of application Ser. No. 09/842,838, filed Apr. 27, 2001 (now U.S. Pat. No. 6,875,617), which is a Continuation-in-Part of application Ser. No. 09/223,738, filed Dec. 31, 1998 (now abandoned), which is divisional of application Ser. No. 08/965,873, filed Nov. 7, 1997 (now U.S. Pat. No. 5,900,376); and a Division of application Ser. No. 09/507,977, filed Feb. 22, 2000 (now abandoned), which is a Continuation-in-Part of application Ser. No. 09/249,499, filed Feb. 12, 1999 (now abandoned), which is a Continuation-in-Part of application Ser. No. 08/965,873, filed Nov. 7, 1997 (now U.S. Pat. No. 5,900,376). The disclosures of these prior applications are hereby incorporated by reference herein in their entirety.

HISTORY OF THE INVENTION

Protein sample containing high concentration of ionic detergents such as SDS can not be successfully used for running iso-electric focusing and 2D gels. For running protein electrophoresis, if the protein solution contains high concentration of salt and some detergents (such as SDS, Triton-X100 etc.), and other agents, these agents interfere and reduce the quality of electrophoresis. When protein solution is very diluted it may be necessary to concentrate the protein solution before running electrophoresis. Many analytical methods therefore require concentration of dilute protein solution and removal of non-protein agents from the protein solution. If a protein solution is concentrated by lyophilizing, the concentration process may also concentrate the non-protein agents present in the protein solution. Protein concentration by precipitation technique has its own limitations; the standard acid treatment precipitation may not be quantitative and result in loss of protein. Furthermore, when protein is precipitated by acid treatment it has the tendency to precipitate other non-protein agents such as detergents present in the protein solution, making the removal of detergents difficult. The acid precipitated protein precipitates contain high concentration of residual acid used for the precipitation, creating solubility problem for downstream processing. Concentration by filtration do not remove non-protein agents present in protein solution. Dialysis on the other hand may remove non-protein agents from protein solution but dialysis do not concentrate protein solution.

There are several protein precipitation methods currently in use, unfortunately, they all suffer from serious limitations. One of the most widely used methods of protein precipitation uses trichloroacetic acid (TCA). When a protein solution is mixed with a solution of TCA, protein precipitates. Unfortunately, TCA induced precipitation of protein is not always quantitative. When TCA is added to a protein solution containing protein whose concentration could be measured in several milligrams per milliliter, most of the protein in solution is indeed precipitated. However, precipitation is not complete and a small amount of protein is left behind in solution that fails to precipitate in response to TCA or other acids. If on the other hand, a protein solution contains only microgram level concentration, the additions of TCA or other acids do not result in protein precipitation, i.e., a very dilute protein solution do not precipitate in response to acids. Furthermore, if a protein solution contains detergent, particularly an anionic detergent such as sodium dodecyl sulfate (SDS), the addition of TCA does not result in protein precipitation. In addition, it is widely know that when protein is concentrated by TCA precipitation method, after TCA acid treatment the solubility of protein precipitate pellet is reduced making is difficult to completely dissolve the protein pellet and achieve desired protein solubilization particularly at higher protein concentration (desired protein solubilization taken to mean protein solution of desired concentration).

Bensadoun and Weinstein ( Anal Biochem. 1976, 70, 241-250.) and Peterson G. L. (Anal. Biochem. 1977. 83, 346-356) have described methods of protein assays based on precipitation of protein in dilute solutions. According to the methods, protein solution is first mixed with a solution of sodium deoxycholate and the mixture of protein and deoxycholate is precipitated by the addition of trichloroacetic acid (TCA). This method of protein precipitation does not work in protein solution containing detergents such as, Triton-X100, sodium dodecyl sulfate, (SDS) and so forth. Polacheck and Cabib (Anal Biochem. 1981, 117, 311-314) have used RNA as a carrier to facilitate precipitation of protein in the presence of detergents. The disadvantage of Polacheck and Cabib method is that precipitation requires a prolonged incubation period in cold followed by prolonged centrifugation at >25,000×g. Furthermore, this method of protein precipitation is not suitable for dilute protein solution containing a high concentration of detergents. Various authors have tried various techniques to improve on Bensadoun and Weinstein method. Retz and Steele. (Anal Biochem. 1977, 79, 457-461) have tried addition of sodium dodecyl sulfate in amount nearly equivalent to that of the detergents present in protein solutions. Yen-Chung Chang (Anal. Biochem. 1992. 205, 22-26) has attempted to improve on the method of Polacheck and Cabib by addition of SDS to achieve detergent/SDS ratios at 0.67. The disadvantage of this method is that in an unknown solution, it is not easy to reach detergent/SDS ratios at 0.67 without additional investigations.

Carraro et. al. (Electrophoresis 1991, 12, 1005-1010 and BioChem and Biohys Res Comm., 1994, 200, 916-924) and Sandri et. al (Anal Biochem. 1993, 213, 34-39) have attempted to use acid and salt mixture to precipitate protein from solutions containing SDS. Carraro el. al had earlier made unsuccessful attempts to develop a one step method of precipitation of protein from a solution containing SDS. According to Carraro et al. and Sandri et al., "at higher SDS levels, large pellets will form, preventing good protein recovery and concentration". Having failed in their attempts to quantitatively precipitate protein from solutions containing SDS they focused their efforts on two step methods with a limited success. They developed a two step method of precipitation of protein, the first step involved precipitation of SDS followed by precipitation of protein. The Carroaro et al. method is essentially a two step method of precipitation of protein from a solution containing SDS, the method is dependent on temperature, pH, the nature of salt, and the concentration of SDS. Carroaro et al method is also dependent on protein-to-protein variations, works only with potassium salts, and recovery is significantly less than 100% (hydropholic and low ionic strength protein are lost). The Carroaro et al. method only works exclusively in the presence of SDS in protein solution and their methods can not be used for other types of detergents, particularly cationic, other anionic, and non-ionic detergents, and other agents such as lipids and natural products.

Organic solvents such as acetone and alcohol have been used for precipitation of protein in aqueous solution. However, precipitation of diluted protein solution with acetone is not quantitative for all protein. There are proteins that do not precipitate with organic solvents. Organic solvent precipitation methods require prolonged incubation period to achieve protein precipitation and some protein even after prolonged incubation do not precipitate. Therefore, organic solvent can not be used to quantitatively precipitate all types of protein.

The advent of proteomic era has heighten the need for preparing protein sample for proteomic works and other analysis, such protein samples must be substantially free from non-protein agents commonly present in most protein preparation. The presence of salts in protein samples disturbs the electrophoretic process. Lipids binding to protein can later electrophoretic separation and gives rise to errors and artifacts. Similarly charged polysaccharides can bind to protein an alter electrophoretic separations. Natural products such as polyphenols, tannins, alkaloids, pigments may bind with protein and give rise to artifacts. Unfortunately, there is still no method that could be universally applied for quantitative precipitation of protein from solutions, irrespectively of the nature of non-protein agents present in the protein solution, as well as make the precipitated protein substantially free from non-protein agents. Furthermore, when dealing with dilute protein solutions, it is important to concentrate the sample to achieve a higher protein concentration so that within the limits of sample volume (for IPG strips) sufficient amount of protein may be loaded on the IEF/2D analysis.

Methods that concentrate protein solution do not remove non-protein agents from solution on the other hand methods that do remove non-protein agents from protein solution do not concentrate dilute protein solution. Therefore, there is a need for developing a method of concentrating protein solution and removing non-protein agents, such as detergents, salts, lipids, natural products, common laboratory agents etc., from protein solution. Method should be rapid and results in quantitative recovery of protein after the procedure. There is also a need for developing a method of protein assay that could overcome interference from non-protein agents present in protein solutions containing detergents.

SUMMARY OF THE INVENTION

The present invention relates to composition of a protein-precipitation agent and the use of the protein-precipitation agent in a method of protein precipitation and a method of preparation of protein sample for analysis such electrophoresis, protein assays etc., wherein the protein sample solution may contains one or more of non-protein agents selected from a group consisting of an anionic detergent, a cationic detergents, a non-ionic detergent, a zwitterionic detergent, a sulfobutane, a lipid, a natural product, a salt, and a common laboratory agent. This invention further relates to a method of concentration of protein solution and removing non-protein agents from the protein solution. The present invention further relates to a method of total protein assay in a sample using a protein-precipitation agent, a method of total protein assays in a sample that overcomes interference by common non-protein agents present in protein solution, and a kit for a total protein assay.

An embodiment of the present invention relates to composition of a protein-precipitation agent and for precipitation of protein in aqueous solution, wherein the protein sample solution may contains one or more of non-protein agents selected from a group consisting of an anionic detergent, a cationic detergents, a non-ionic detergent, a zwitterionic detergent, a sulfobutane, a lipid, a natural product, a salt, and a common laboratory agent.

A protein precipitation-agent, comprising: an acidic component (agent) and one or both agents selected from a group consisting of a salt and a precipitate forming agent.

Said salt is an agent selected from a common salt, a detergent-precipitation agent, protein salting out agent or a soluble salt. Wherein the detergent-precipitation agent is an agent that precipitates detergent in aqueous solution and a protein salting-out agent is a salt agent that precipitates protein in aqueous solution (such as ammonium sulfate, sodium chloride, ect.). For convenience, detergent-precipitation agent, protein salting out agent or a soluble salt are refereed to as a salt.

Preferably the detergent-precipitation agent (salt) is a sodium, potassium, or other salt agents such as gunidine salts that precipitate a detergent in aqueous solution. Preferably, the concentration of salt provided in the protein-precipitation agent is high enough to precipitate the detergent (such as SDS) or protein. For sodium salts the concentration to precipitate SDS is higher than 0.4M salt.

Preferably the salt is added into the acidic component. Preferably, the concentration of salt is higher than 0.1M and most preferably the salt concentration is between 1-5M or substantially close to reaching a saturation salt concentration.

Said precipitate-forming agent is an agent that readily forms precipitate in the presence of said acid component (agent). The precipitate-forming component are those agents that readily forms precipitate (i.e. turns into precipitate when come in contact with the acid agents) when come in contact with the acidic component of the protein-precipitation agent of the instant invention. The precipitate-forming components may be selected from agents such as sodium benzoate, sodium cholate, sodium deoxycholate, or other agents that readily form precipitate in the presence of the acidic component (agents). Other salt forms of deoxycholate, cholate, and salts, particularly monovalent salts of organic acids which precipitates in acidic medium may be used as precipitate-forming agents, for example sodium salt of uric acid. The claimed invention describes a few precipitate-forming agents, however, there are other agents that readily form precipitate in the presence of acidic component and thus may be used as precipitate-forming agent.

The acidic component may be selected from organic or inorganic acids such as trichloroacetic acid (TCA), sulfosalicylic acid, hydrochloric acid, sulfuric acid, perchloric acid, and other acidic agents that substantially lower the pH toward acidic. It should be appreciated that the specification lists a few well known acidic agents, however, other types of acidic agents may be used.

A method of protein precipitation comprising, treating the protein solution, preferably but not exclusively containing one or more of non-protein agents selected from a group consisting of an anionic detergent, a cationic detergents, a non-ionic detergent, a zwitterionic detergent, a sulfobutane, a lipid, a natural product, a salt, and a common laboratory agent, with a protein-precipitation agent, said protein-precipitation agent comprising an acidic agent and one or both agents selected from a group consisting of a salt and a precipitate forming agent, wherein the treatment of the protein with the precipitate-forming agent follows the treatment of the protein with the acidic agent.

A yet another embodiment of the present invention relates a to protein-precipitation agent comprising: an acidic component (agent) and a salt agent.

Said protein-precipitation agent may also be provided with a precipitate-forming agent (component).

A method of protein precipitation comprising, treating the protein solution, preferably but not exclusively containing one or more of non-protein agents selected from a group consisting of an anionic detergent, a cationic detergents, a non-ionic detergent, a zwitterionic detergent, a sulfobutane, a lipid, a natural product, a salt, and a common laboratory agent, with a protein-precipitation agent, said protein-precipitation agent comprising an acidic agent and a salt. Preferably, after treating the protein solution with the protein-precipitation agent the mixture of the protein and the protein-precipitation agent is treated with a precipitate-forming component.

After a protein precipitate is formed, protein precipitate may be collected (harvested) either by centrifugation or by filtration means and used for protein assay or other uses.

A yet another embodiment of the present invention relates to composition of a protein precipitation agent and a method of precipitation of protein in aqueous solution.

A protein-precipitation agent comprising: an acidic component (agent) and a precipitate-forming component (agent), wherein said precipitate-forming component is an agent that readily forms precipitate (i.e. turn into precipitate) in the presence of said acidic component.

Preferably, the protein-precipitation agent may also contain a soluble salt. Preferably the salt is added into the acidic component. Preferably the salt present in the protein precipitating agents is a sodium, potassium or other common salt. Preferably, the concentration of salt provided into the protein precipitation agent is higher than 0.1M and most preferably the salt concentration is between 1-5M or substantially close to reaching a saturation salt concentration.

A method of protein precipitation comprising: introducing an acidic component into the protein solution followed by introduction into the mixture of protein and the acidic component a precipitate-forming component, wherein said precipitate-forming component is an agent that rapidly forms precipitate when come in contact with the mixture of protein and the acid component.

Preferably, the mixture of protein and the acidic component is provided with a soluble salt to encourage protein precipitation. Preferably the salt introduced into the mixture of protein and the acidic component is sodium, potassium or other common salts. Preferably, the concentration of salt is higher than 0.1M, and more preferably between 1-5M or substantially close to reaching a saturation salt concentration.

After a protein precipitate is formed, protein precipitate may be collected either by centrifugation or by filtration means and used for protein assay or other uses.

A yet another embodiment of the invention relates to a method of removing detergents and other non-protein agents present in the protein solution, comprising: treating the protein solution with the protein-precipitation agent of the present invention, harvesting the precipitated protein and the removal of protein free supernatant. The harvested precipitated protein is suspended and washed with an organic solvent. Preferably, prior to washing the protein precipitate with the organic solvent, the protein precipitate may be first suspended in a small volume of aqueous medium such as pure water and then organic solvent is added. Alternatively, the protein precipitate is suspended in a mixture of water-organic solvent. The organic solvent may be selected from acetone, alcohol, and other organic solvents miscible in water. Preferably, the precipitate-forming agent of the protein-precipitation agent is soluble and extractable in the organic solvent used for washing the precipitated protein.

Yet another embodiment of the present invention relates to a method of protein assay.

A method of total protein assay, comprising the following steps:

(a) treating a protein solution with a protein-precipitation agent, said protein-precipitation agent comprising an acidic component and a salt;

(b) collecting the protein precipitate formed as a result of the treatment of step (a); and (c) combining the collected protein precipitate of the step (b) with one or more reagents of a protein assay to produce a characteristic protein color reaction, wherein the reagent for protein assay is alkaline in nature and has alkali in amount sufficient to neutralized the acids captured in the protein pellet.

Preferably, after treating protein solution with the protein-precipitation agent of step (a) the mixture of protein and protein-precipitation agent may be treated with a precipitate-forming component. The precipitate-forming component are those agents that readily form precipitate when come in contact with the acidic component of the protein-precipitating agent of the instant invention. The precipitate-forming components may be selected from agents such as sodium benzoate, sodium cholate, sodium deoxycholate, or other agents that readily form precipitate in the presence of the acidic component (agents). Other salt forms of deoxycholate, cholate, and salts, particularly monovalent salts of organic acids which precipitates in acidic medium may be used as precipitate-forming agents, for example sodium salt of uric acid. The claimed invention describes a few precipitate-forming agents, however, there are other agents that readily form precipitate in the presence of acidic component and thus may be used as precipitate-forming agent. Preferably, the precipitate-forming agent (component) is soluble in the organic solvents.

Protein concentration is determined by measuring the density of the protein color reaction and comparing the color density with the color density of protein color reaction of a known protein concentration or protein standard.

A further embodiment of the present invention relates to a kit for protein assay comprising: a protein-precipitation agent; and one or more reagents of a protein assay to produce characteristic protein reaction.

PREFERRED EMBODIMENT OF THE INVENTION

Figure 1:
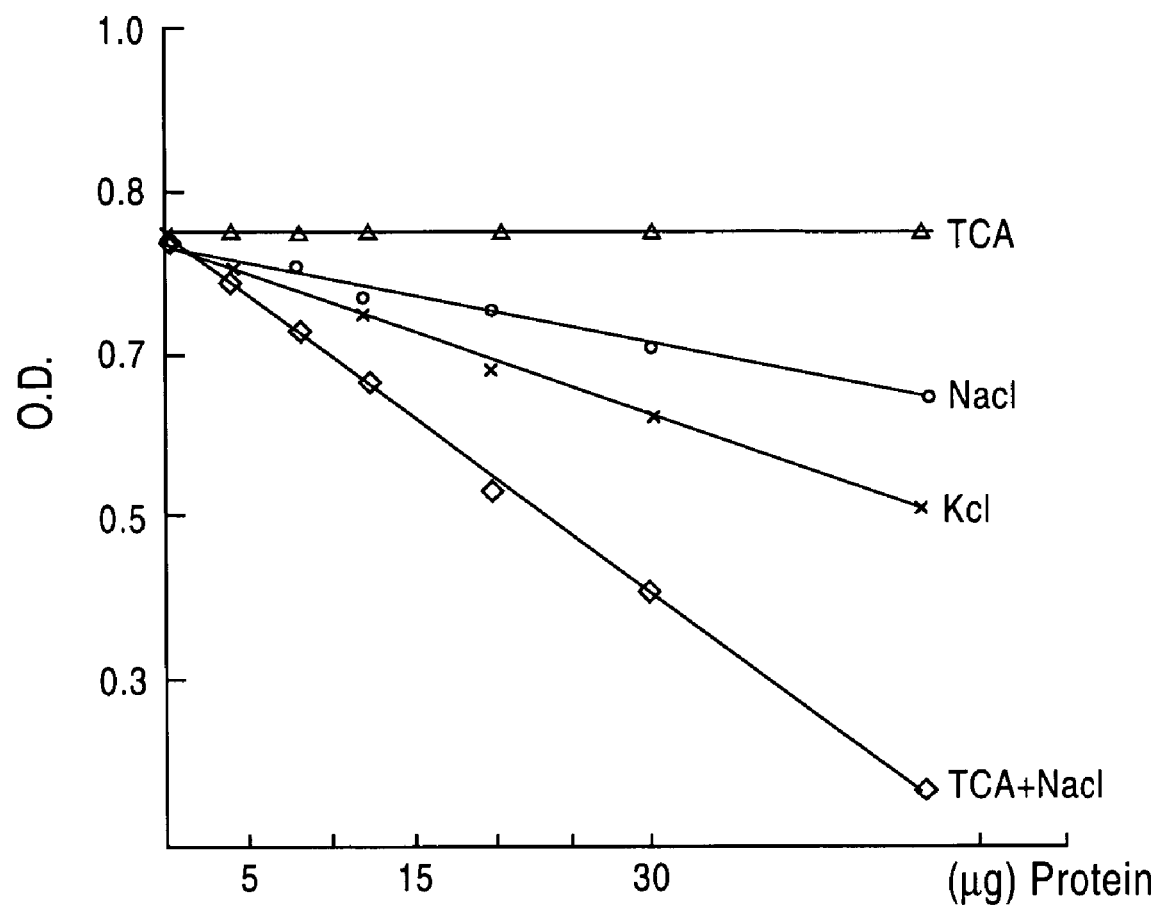
FIG. 1 shows precipitation characteristic of protein solution containing SDS when treated with acidic component TCA with and without a detergent-precipitation agents (a salt). A 4M solution of sodium chloride and 0.2M potassium chloride were used as detergent-precipitation agents. 10% TCA was used as acidic component/agent. The protein-precipitation agent containing 10% TCA and 4M NaCl was used.

The novelty of the instant invention may be appreciated from the following facts. Protein readily binds to anionic detergent deoxycholate. Deoxycholate readily precipitates in the presence of acids such as trichloroacetic acid (TCA). Thus, protein bond to deoxycholate is readily precipitated with an acid. Here, the binding of protein to deoxycholate is essential for protein precipitation. However, when a dilute protein solution contains another anionic detergent such as SDS, the addition of TCA does not precipitate protein. If a deoxycholate is added to a protein solution containing SDS, and then a TCA solution is added, there is still no protein precipitate formation. If on the other hand, a dilute protein solution containing SDS is treated with a dilute solution of TCA containing an effective concentration of sodium or potassium salts, protein quantitatively precipitates.

The novelty of the instant invention is further reinforced from the following facts. Organic solvents such as acetone has been used for precipitation of protein in aqueous solution. This method suffer from a serious limitation, dilute protein solutions containing micro or nanog-gram levels of protein is not efficiently and quantitatively precipitated with acetone or other organic solvents. Often acetone precipitation of dilute protein solution requires prolonged incubation ( several hours of incubation) and even after prolonged incubation not all protein is quantitatively precipitated. There are proteins that do not precipitate with organic solvents such as acetone. Therefore, acetone precipitation can not be used as a universal protein precipitation agent.

According to the present invention there is provided an agent for protein-precipitation. A protein precipitating agent comprising: an acidic component (agent) and a precipitate-forming component (agent), wherein said precipitate-forming component readily forms precipitate when come in contact with said acidic component.

The protein-precipitation agent may also contain one or more soluble salts, salts such as sodium, potassium, calcium, magnesium, sodium sulfate, or other common salts. Most preferably, the salt used in protein precipitating agents is sodium chloride. The salt may be added either into the acidic component or into the precipitate-forming component or into both components of the protein precipitating agent (i.e., both acidic and precipitate-forming components). Most preferably, the salt is added into the acidic component (agent) of the protein precipitating agent. The concentration of salt added into the protein precipitating agents is preferably higher than 0.1 M. Most preferably the concentration of salt added into the protein precipitating agents is between 1-5 M or substantially close to reaching saturation salt concentration.

According to the present invention there is also provided a method of protein precipitation and preparation of protein sample for analysis, comprising: mixing a protein solution with an acidic component; and then introducing a precipitate-forming component into the mixture of protein and the acidic component. When an acidic component is introduced into a protein solution, the mixture of the protein and the acidic component is preferably incubated for a length of time, preferably for 1-10 minutes. Upon introduction of said precipitate-forming component into the mixture of the protein and the acidic component, the protein in solution rapidly co-precipitate with the precipitates-forming component. Precipitate may be collected or harvested from the solution either by filtration or by centrifugation. Preferably, for recovery of the protein pellet the solution is centrifuge to form a tight pellet at the bottom of the tube, the supernatant is remove and discarded. Any residual supernatant is removed by a second centrifugation followed by extraction of the residual supernatant with a pippet tip (i.e., a tipped suction device).

Without being bound to any particular chemical principle of protein precipitation, Applicants believe that when a dilute protein solution is treated with an acidic component, such as TCA, sulfosalicylic acid and similar agents, the protein in solution is converted to colloidal particles and such colloidal particles are not easy to precipitate. Addition of a precipitate-forming component into the mixture of a protein and an acidic agent aggregates the colloidal protein particles into larger particles which consequently co-precipitate with the precipitate-forming component.

According yet another embodiment of the present invention there is provided a protein-precipitation agent. Said protein-precipitating agent comprising; an acidic component (agent) and a salt agent (component), wherein the salt agent is at a concentration effective to precipitate detergent and/or protein in the protein solution.

The salt agents are those agents that readily precipitates detergent, or salt-out (precipitate) protein in aqueous solution. The detergent-precipitating (salt) agent is preferably one or more soluble salts, salts such as sodium, potassium, calcium, magnesium, sodium sulfate, or other common salts and agents such as guanidine hydrochloride. Sodium salts at concentration higher than 0.4M precipitate detergent SDS in aqueous solution. Whereas potassium salt precipitates SDS even at micro molar concentration. Most preferably, the salt used in protein-precipitation agents is sodium chloride. The salt may be added either into the acidic component or used separately. The mixture of acidic component and detergent-precipitation agent is termed protein-precipitation agent.

Most preferably, the detergent-precipitation (salt) agent is added into the acidic component. The concentration of detergent-precipitation agent should be high enough to precipitate detergent in aqueous solution. The concentration of detergent-precipitation agent NaCl added into the protein-precipitating agents is preferably higher than 0.4 M. Most preferably the concentration of detergent-precipitation agent NaCl provided into the protein-precipitating agents is between 1-4 M.

According to the present invention there is also provided a method of protein precipitation comprising; treating protein solution with a protein-precipitation agent, said protein-precipitation agent comprising an acidic component and a salt.

When a protein solution is treated with protein precipitation agent, the mixture is preferably incubated for a length of time, preferably for 1-10 minutes. Precipitate may be collected or harvested either by filtration or by centrifugation.

According to another embodiment of the invention, there is provided a method of preparation of protein sample and removing non-protein agents, such as agents selected from a group consisting of an anionic detergent, a cationic detergents, a non-ionic detergent, a zwitterionic detergent, a sulfobutane, a lipid, a natural product, a salt, and a common laboratory agent, detergents, salts, acids and other agents present in protein solution. Precipitation of protein with organic solvent is neither always guaranteed nor quantitative and also it requires prolonged incubation. Protein when precipitated with acidic agent, many detergents co-precipitate with protein in the solution. According to the present invention, the protein solution is first precipitated using the protein-precipitation agent of the instant invention and the supernatant containing non-protein agents is removed from the precipitated protein. Any non-protein agents co-precipitated or otherwise present in the protein precipitate is remove from the precipitated protein using a water miscible organic solvent such as alcohol or acetone. Before treating the protein precipitate with the organic solvent, it is preferably to first suspend the protein precipitate in a small volume of aqueous medium such as water, which allows the extraction of residual water soluble agents such as salts and acids into the aqueous medium. The volume of aqueous medium added in to the protein precipitate should not be such or larger enough to significantly shift the acidity of the protein-precipitate suspension and solubililize the precipitated protein. Alternatively, the protein precipitate is suspended in a mixture of water(aqueous)-organic solver (acetone). The protein precipitate may be further suspended in organic solvent or the mixture of water-organic solvent. The organic solvent used for washing the protein precipitate is such that it extracts non-protein agents such as detergents or other agents from the protein precipitate into the organic solvent. Acetone and alcohol both can extract ionic as well as non-ionic detergents and many other agents from the protein precipitate and thus preferred. If the protein-precipitation agent contains a precipitate forming agent, the precipitate-forming agent should preferably be soluble and extractable in the organic solvent used for washing the protein precipitate. Other organic agents may also be used in place of acetone and alcohol. However, acetone is preferred over alcohol because of faster rate of evaporation. After washing the protein precipitate with the organic solvent, the precipitate is dried and reconstituted in a aqueous medium of choice.

Yet another embodiment of the present invention relates to a method of protein assay comprising the following steps:

treating protein solution, preferably containing one or more of non-protein agents selected from a group consisting of an anionic detergent, a cationic detergents, a non-ionic detergent, a zwitterionic detergent, a sulfobutane, a lipid, a natural product, a salt, and a common laboratory agent with a protein-precipitation agent, said protein-precipitation agent comprises an acidic agent and a salt;

collecting the precipitate formed as a result of the treatment with protein-precipitation agent; and mixing the collected precipitate with one or more reagents of a protein assay to produce a characteristic protein reaction, preferably a color reaction.

Protein concentration is determined by reading the optical density of the protein color reaction and comparing the color density of the protein color reaction with the color density of a protein reaction of known protein concentration. Protein concentration may also be determined by measuring spectral changes in protein solution or measuring the optical density of protein solution, without any visible color, such as measuring the optical density of protein solution in ultra violet range, such as at 280 nm.

Preferably, the protein-precipitation agent is a mixture of acidic agent (component) and a salt protein-precipitation agent may be prepared by keeping the acidic agent separate from the salt and adding the two agent into protein solution one after another in and order. Most preferably, the protein-precipitation agent is a mixture solution of acidic component provided with a salt at a concentration effective to precipitate the detergent in aqueous solution.

The salt agent may be selected from a group comprising; sodium, potassium, magnesium or other common salts. Preferably, the salt used in the protein precipitating agents is a sodium salt, preferably, sodium chloride. The concentration of salt (NaCl) provided into the mixture of protein and the acidic component (i.e. protein-precipitation agent) is preferably higher than 0.4M. Preferably, the concentration of salt (NaCl) provided into the mixture of protein and protein precipitation agent is between 1-4M.

For a protein assay, after collecting protein precipitate (following the addition of a protein-precipitation agent), the precipitate is preferably dissolved in an aqueous solution. Preferably, the protein precipitate is dissolved in an alkaline solution. The alkaline solution preferably containing a copper salt, preferably a copper sulfate. For a protein assay, a second protein assay reagent may be introduced into the mixture of protein-alkaline copper. The second protein assay reagent may be selected form a group consisting of; Folin reagent or bicinchoninic acid derivatives, and bathocuproine, to produce a characteristic protein color reaction.

Yet another embodiment of the present invention is a kit for protein assay comprising:

a protein-precipitating agent; and one or more reagents of a protein assay.

Said protein-precipitating agent comprising an acidic component and a salt. The salt added to the protein precipitating agent may be selected from a group, comprising; sodium, potassium, other common salts. Preferably, the salt provided into the protein precipitating agent is a sodium salt, most preferably sodium chloride. The salt, NaCl is preferably added into the acidic component, at a concentration higher that 0.4M, and most preferably at a concentration between 1-5M.

EXAMPLES

The invention is further explained with the help of the following examples.

Materials and Methods:

Protein Solution: A protein assay was performed as follows. Unless indicated otherwise, 2 mg/ml BSA protein solution in distilled water was used in this study. Unless specified otherwise, aliquots of 1-30 µl were transferred in to (2 ml) microfuge tubes. An appropriate volumes of non-protein agents (such as detergents, reducing agents, chelating agents etc) were added to the protein samples and mixed, which created a mixture of protein solution in the presence of, detergent and non-protein and/or interfering agents. In control, protein solution was not mixed with any non-protein agent, instead 100 µl pure water was added to each tube. When indicated, the protein solution used in this study was other than BSA. When indicated, an appropriate volume of 1% solution of SDS was use to treat protein solution with SDS.

Protein Assay agents: The methods of present inventions were tested using popular protein assay reagents. The tests were performed using a modification of the Lowry protein assay method (Lowry et al., J. biol. Chem., 1951, 193, 265-275) as modified and described in the U.S. Pat. No. 5,300,440, a bicinchoninic acid method of a protein assay as described by Smith et al (Anal. Biochem. 1985, 150, 76-85), and an alkaline copper -bathocuproine based protein assay as described by (Matsushita et. al. Clinica Chimica. 1993, 216, 103-111).

The reagents of the Lowry method of protein assay included: An alkaline copper solution containing a copper salt (0.05%) and sodium-potassium tartrate (0.16%) in a sodium hydroxide solution (1N), hereinafter refereed to "alkaline copper solution" and a solution of Folin-Ciocalteu reagent (5-15%).

The bicinchoninic acid method consisted of a solution A, 1% bicinchoninic acid sodium salt, 2% sodium carbonate, 0.16% sodium tartrate, 0.4% sodium hydroxide, and 0.95% sodium bicarbonate, pH 11-12. A solution B: consisted of 4% copper sulfate. Before use the solution A and B were mixed in 100 part solution A and 2 part solution B (i.e. 100:2), hereinafter referred to as "alkaline copper solution".

Copper-bathocuproine protein assay method consisted of a Solution A containing copper sulfate (0.05%) and tartrate (0.16%) in NaOH (1N), hereinafter, refereed to "alkaline copper solution". A solution-B, a color producing solution containing ascorbic acid (1.4 mM, 250 mg/L) and bathocuproine (0.65 mM, 370 mg/L bathocuproinedisulfonic acid sodium salt).

Protein-precipitation agents: Unless specified, protein precipitation agents was made by mixing an acidic agent (component) and a salt in a solution. When specified the protein-precipitation agent only contained acidic agent and no salt was added to it.

Acidic component: selected form a group consisting of a 1-10% solutions of trichloroacetic acid, sulfosalicylic acid, and hydrochloric acid (0.01-2N). acidic component.

Salt agent: selected form a group consisting of a sodium and potassium chloride salts, in concentration 0.2M-4M.

Precipitate-forming component: selected form a group consisting of a 0.01-3% solutions of sodium deoxycholate, sodium cholate and sodium benzoate were used as precipitate forming agents Protein Treatment: For protein precipitation, an appropriate volume of protein-precipitation agent was introduced into the protein solution and mixed. A massive precipitate was observed.

The precipitates were collected (harvested) by either filtration (using spin or disk filters) or by centrifugation. When a centrifugation was used to collect the protein precipitate, the precipitate was separated from the supernatant by decanting off the supernatant. Preferably, for recovery of the protein pellet the solution was centrifuge to form a tight pellet at the bottom of the tube, the supernatant was remove and discarded. Any residual supernatant was removed by a second centrifugation followed by extraction of the residual supernatant with a pippet tip (i.e., a tipped suction device).

For protein assays, the protein assay reagents were directly added to the precipitate as described in various examples. Alternatively, precipitate may be dissolved into an aqueous solution, followed by the addition of the reagent of a protein assay, wherein the reagent of protein assay is alkaline and has alkali in amount sufficient to neutralize the acid captured in the protein pellets.

For a protein assay, the assay reagents may be directly added to the precipitate as described in various examples. Alternatively, the precipitate may be first dissolved in an aqueous solution, followed by the addition of one or more reagents of protein assays.

For a protein assay based on the Lowry method, the precipitate was preferably directly dissolved in the alkaline copper solution ( of the Lowry method), followed by the addition of the Folin reagent.

For a protein assay based on the bicinchoninic acid method, the precipitate was preferably directly dissolved in the alkaline copper solution (of the bicinchoninic acid method).

For a protein assay based on the copper-bathocuproine method, the precipitate was preferably directly dissolved in the alkaline copper solution (of the copper-bathocuproine method).

SDS-Gel Electrophoresis

The protein solution and the precipitated protein pellets were analyzed by SDS-polyacryalminde gel electrophoresis using a well know Laemmli method. In brief, protein test samples or protein precipitates were treated with sample loading buffer (0.062 mM Tris, pH 6.8, 2% SDS, 5% 2 ME and bromophenol blue) and heat treated for 5 minutes in boiling water. Samples were subjected to electrophhoresis on 4-20% SDS-gradient polyacryamide gels. The protein bands were developed by staining the gel with Coomassie dye.

Example 1

The effectiveness of the various elements of protein-precipitation agent was tested. Solution of TCA (10%) was used as acidic component and sodium chloride and potassium chloride were used as a salt (detergent-precipitation) agents.

Aliquots of 2-30 µl from a standard protein solution (2 mg/ml BSA ) were transferred to four series of microfuge tubes. 100 µl of 1% SDS was added to each tube and mixed. A 0.1 ml aliquot of the 4M NaCl, 0.2M KCl, 10% TCA, and protein-precipitation agent (a 10% TCA solution containing 4M NaCl) were introduced into the test protein solutions and immediately mixed by vortexing the tubes.

A large amount of precipitate was observed in each tube, except for the tube treated with solution containing only 10% TCA solution. Precipitates were collected by centrifuging the tube at 5000×g for 5 minutes. Supernatant was removed by inverting the tube on a clean absorbing paper. The precipitate pellets were firmly attached to the bottom of the tubes.

Protein assays: The effectiveness of various agents to precipitate protein was determined by a protein assay method, as follows. 100 μl of alkaline copper solution (1N NaOH containing 0.05% copper sulfate and 0.16% tartrate) was added to each precipitate, after mixing, 0.4 ml of pure water was added to each tube and mixed. 1.0 ml of color producing agent (bathocuproine) was introduced into each tube which produced a characteristic light orange color for protein reaction. The optical density of each tube was determined at 480 nm. The optical density of each tube was plotted against the amount of protein added to each tube. Results are shown in FIG. 1.

FIG. 1 shows protein solution cotaining SDS did not precipitate effectively when treated only with a 10% TCA solution (no salt added). NaCl and KCl alone did precipitate protein but the precipitation was not quantitative, some protein was lost during precipitation and not recovered after centrifugation. However, TCA solution containing 4M NaCl effectively precipitated protein and 100% protein was recovered after centrifugation ( data matches with control which was not subjected to any precipitation, see FIG. 3)

The result clearly indicates that the protein-precipitation agent (containing an acidic component TCA and NaCl as detergent-precipitation agent, effectively and quantitatively precipitate protein in solution over a wide range of protein concentration.

In subsequent experiments (Examples 2-13), protein solutions were treated with the protein-precipitation agent containing 10% TCA and 4M NaCl, except when indicated otherwise.

Example 2

The effectiveness of various acidic components was tested. Trichloroacetic acid (5-10%), sulfosalicylic acid (5%), and hydrochloric acid (0.7N) were tested as acidic component. 4M sodium chloride was added to each acidic component.

Figure 2:
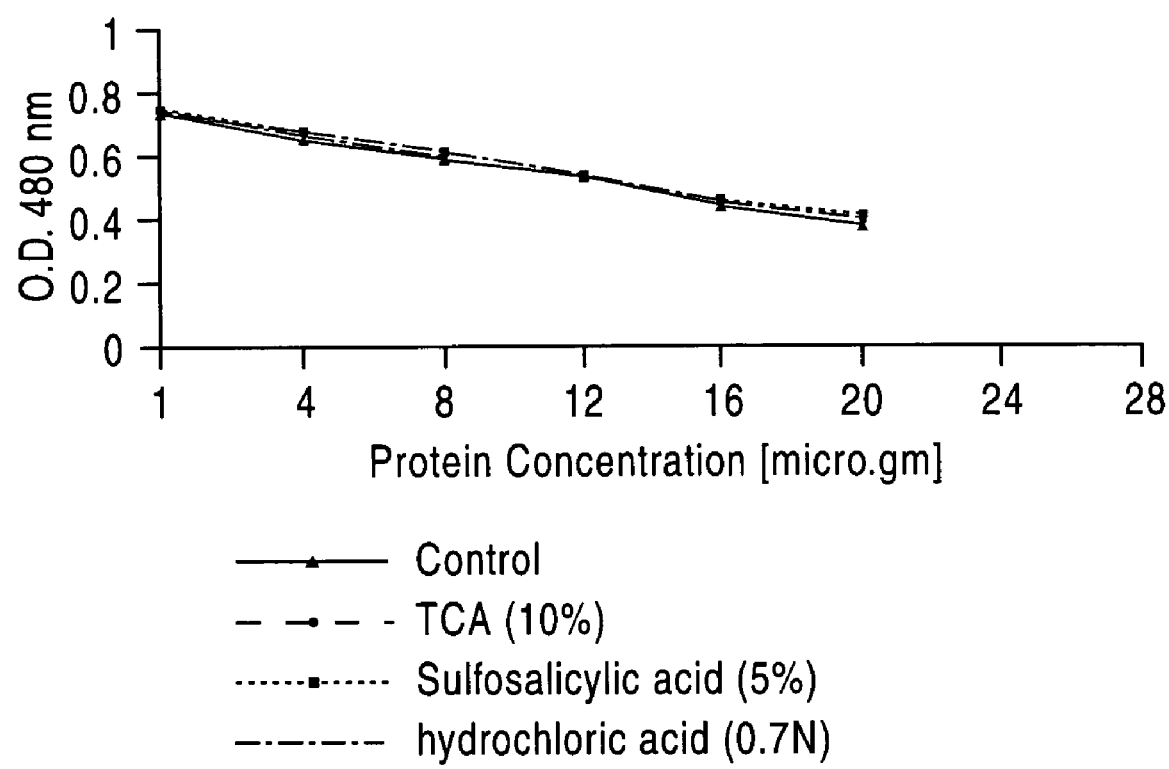
FIG. 2 shows effectiveness of various acidic components used in a protein-precipitation agent.

The tests were performed as described in the Example 1, except TCA, sulfosalicylic acid and hydrochloric acid were used as acidic component. The results are shown in FIG. 2, which established that over a wide range of protein concentration the acidic component tested were effective in quantitative precipitation of protein. Tests were also performed using lower concentration of the acidic agents listed, it was found that concentration as low as 1% TCA was able to effectively precipitate protein (data not shown). However, when protein solution contained a high concentration of non-ionic detergents such as Triton-X100, TCA concentration higher than 3% was needed for quantitative precipitation of protein. Similar results have been obtained with the protein-precipitation agent containing a precipitate-forming agent.

Example 3

The effectiveness of protein-precipitation agents in the presence of detergents such as sodium dodecyl sulfate (SDS) and Triton X100 was tested, and compared with a control protein solution without any detergent. Tests were performed as described in the Example 1. TCA (10%) containing 4M NaCl was used as protein-precipitation agent. Test protein samples were mixed with 100 μl of SDS (1%) and 100 μl of Triton X100 (3%). The control in the test was not treated with precipitation agent.

Figure 3:
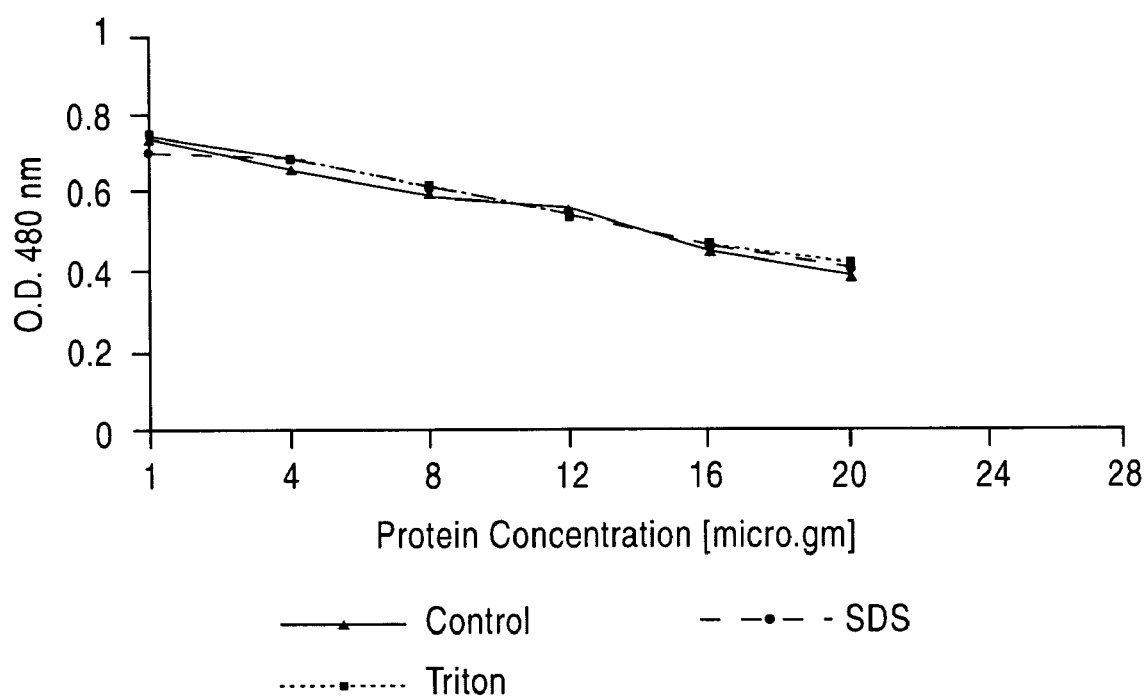
FIG. 3 shows effectiveness of protein-precipitation agents in the presence of detergents

The results are shown in FIG. 3. which establishes that, over a wide range of protein concentration, (as low as 1 ug protein) the protein-precipitating agent is effective even in the presence of high concentration of anionic and non-ionic detergents. A wide range of other detergents were also tested. Protein solutions containing (1-3%), Thesit, CHAPS, CHAPSO, Tween-20, Brij 30, Triton-X114, Sarcosyl, N-Octyl Glucoside, degitonin etc. have been effectively and quantitatively precipitated using the precipitation agent and as described in the instant invention.

The effectiveness of providing a salt in an acidic component was tested. The tests were performed as described above. TCA (10%). An appropriate amount of NaCl was added to protein sample and protein samples with or without detergents (SDS and Triton X100). It was discovered that protein solution without detergent did not require addition of a salt for quantitative precipitation over a wide range of protein precipitation. However, in protein solutions containing high concentration of detergents, the addition of salt in acidic components improved quantitative precipitation of protein. Salt concentration in the range of 1-5M was found to be suitable in most cases.

Similar results have been obtained with the protein-precipitation agent containing a precipitate-forming agent.

Example 4

The effective concentration of detergent-precipitation (salt) agent was tested. The tests were performed as described above in Example 1. TCA (10%) and containing various concentration of sodium chloride and potassium chloride was used (FIG. 5-6).

Figure 5:
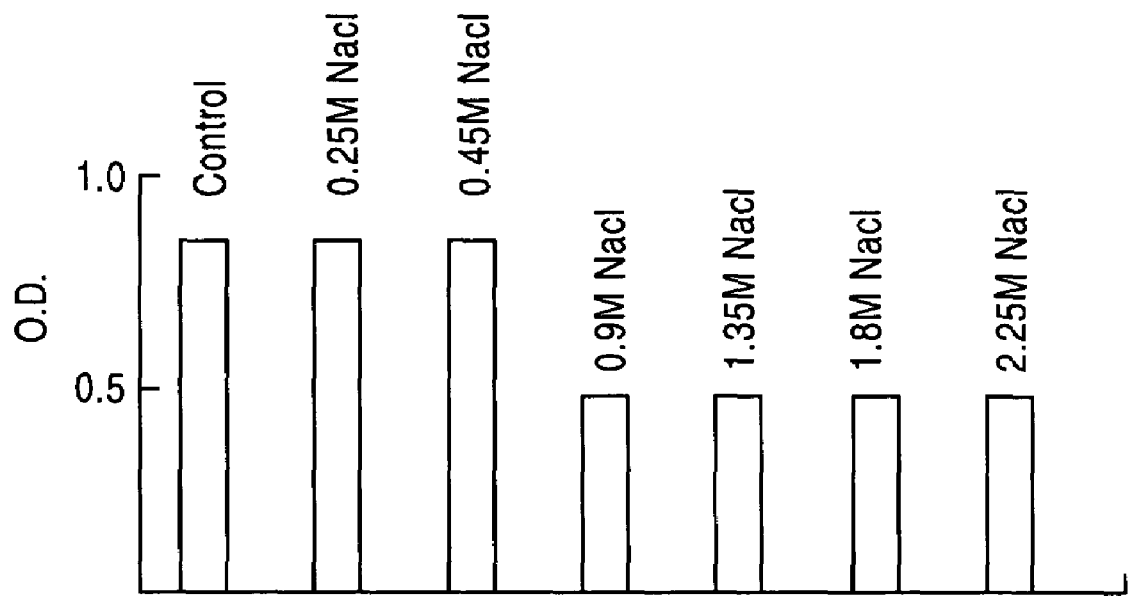
FIG. 5 shows precipitation of protein at different concentration of sodium salt and compared with a control.
Figure 6:
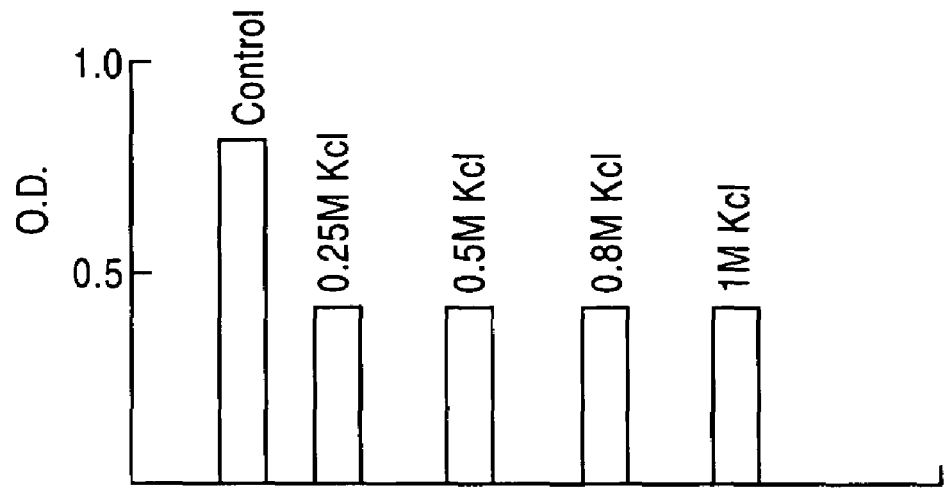
FIG. 6 shows precipitation of protein at different concentration of potassium salt and compared with a control.

It was notice that for NaCl the effective concentration for precipitation of detergent and protein was higher than 0.45 M (FIG. 5). FIG. 5 shows when the concentration of NaCl dropped below 0.9M to 0.45M, the protein did not precipitate and lost when the test sample tubes were decanted to remove supernatant. The optical density is identical to the optical density of control without any protein added to it. NaCl is know to precipitate SDS at concentration higher that 0.7M. For potassium salts even much lower concentration (0.2M) precipitated the protein solution, FIG. 6. Potassium salts are know to precipitate SDS even at a micro-molar concentration, therefore, even lower concentration of potassium can be used a detergent-precipitation agent.

Example 5

The effectiveness of various salts in protein precipitating agents was tested. Tests were performed as described in Example 5. Potassium chloride, sodium chloride, sodium sulfate, magnesium chlorides, zinc etc. have been tested. It was found that most common salts can be used as detergent-precipitation (salt) agent. However, it is important to use an effective concentration, i.e. a concentration at which detergent (SDS) or protein is effectively precipitate in aqueous solution.

Example 6

The effectiveness of protein precipitating agents in removing non-protein agents present in protein solution was tested. The non-protein agents were selected from those agents that are known to interfere with popular protein assays. The tests were performed as described in Example 1. The following agents were tested (by introducing into test protein solution). It was discovered that the protein-precipitation agent of the instant invention effectively precipitated the protein and removed the non-protein agents present in protein solution, which consequently resulted in protein assays free from interference by non-protein agents. The agents tested included urea (8M), 0.5% mercaptoethanol, DTT, guanidine hydrochloride (6), guanidine thiocyanate (6), sodium azide, glycerine, Tris-buffer, EDTA, Hepes, glycine, and a few combinations of these agents such as solution containing urea (4M), SDS and mercaptoethanol and solution containing guanidine thiocyanate, sarcosyl and mercaptoethanol.

In tests described above, successful protein assays were performed without any interference from the agents listed above.

Example 7

Test of reagents of various protein assay methods. The precipitating agent of the instant invention has been used in a various protein assay. Tests were performed as described in Example 1. After collecting protein precipitate, the precipitates were directly dissolved in the alkaline copper solutions of various protein assay methods, as described above in Material and Method section. After dissolving protein precipitate in the alkaline copper solution, an appropriate second protein assay reagent was introduced into the mixture of protein and alkaline copper solution. The second protein assay reagents were selected from a group consisting of Folin, Bicinchoninic acid and bathocuproine. The protein assay worked without any difficulty. A linear response between protein concentration and the optical density was observed (data not shown).

Example 8

Figure 4:
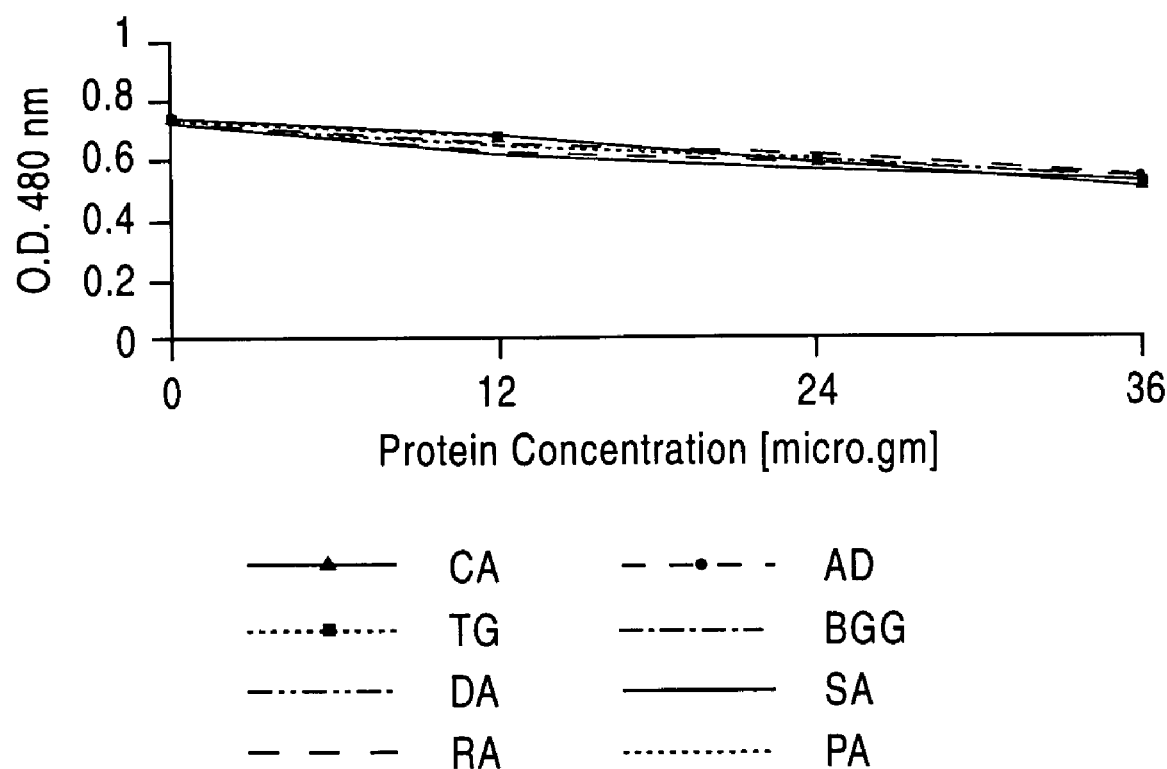
FIG. 4 shows precipitation of a wide variety of protein over a wide range of protein concentration. Furthermore, protein assays do not show protein-to-protein variation.

The effects of a protein precipitating agent on various purified proteins. The following purified proteins have been tested. They are alchohal dehydrogenase (yeast) (AD), carbonic anhydrase (CA), thyroglobulin (TG), dog albumin (DA), sheep albumin (SA), rabbit albumin (RA), and ribonuclase (RN), and bovine gamma globulin (BGG). The tests were performed as described in Example 1, using 10% TCA containing 4M NaCl as protein-precipitation agent. Results are shown in FIG. 4. It was found that the precipitating agent of the instant invention precipitated these protein quantitatively over a wide range of protein concentration. Furthermore, the resulting protein assay showed no protein-to-protein variation. Similar results have been obtained with the protein-precipitation agent containing a precipitate-forming agent.

Example 9

Electrophoretic analysis of protein solution before and after treatment with a protein-precipitation agent.

The effectiveness of protein-precipitation using the instant invention was examined using electrophoreis. The protein-precipitation agent containing TCA (10%) as acidic component and sodium chloride (4M) as a salt agent was used. Aliquots of 4 µl from a mouse liver homogenate (1.18 mg protein/ml) were transferred to a series of microfuge tubes. The protein aliquots were treated in duplicate with 100 µl of 1% solution of various detergents ,( SDS, Triton-X100, Triton-X114, Thiodiglycol, Twee-20, Brij-30, NP-40, CHAPSO, CHAPS, Isotridecylpoly (ethylene-glycolether)$_n$, Thesit, MEGA-8, MEGA-10, N-dodecyl-β-D-maltoside, n-dodecylglucoside, and N-dedecyl-N-N-demethhyl-3-ammonio-1-propane sulfonate). A control sample was also prepared which was not treated with any procedure. After mixing with the detergents solution (final protein concentration 11.18 ng/ml), the protein solutions were precipitated by mixing with 300 µl of the protein-precipitation agent. The precipitate was harvested and collected by centrifugation at 15,000×g for 5 minutes. Preferably, for recovery of the protein pellet the solution was centrifuge to form a tight pellet at the bottom of the tube, the supernatant was remove and discarded. Any residual supernatant was removed by a second centrifugation followed by extraction of the residual supernatant with a pipett tip (i.e., a tipped suction device). The supernatant was removed and the pellets were suspended in small volume of (25 µl) pure water and the tubes were vortex. The addition of water to the protein pellets allowed extraction of the residual acid, salt and other water soluble agents into the aqueous phase. Alternatively, the protein precipitate is suspended in a mixture of water (aqueous)-organic solver (acetone). The protein precipitate may be further suspended in organic solvent or the mixture of water-organic solvent.

Acetone pre-chilled at −20° C. was added to each tube (1 ml) and mixed. The mixture was incubated at −20° C. for 15-30 minutes. In some experiments a small volume (5-6 µl) of (1.5%-2%) solution of a polysaccharide (starch) was added to the solution for the formation of a visible pellets in the tubes. The starch solution may be added to the protein pellet prior to the addition on acetone. The tubes were centrifuge for 5 minutes and the acetone supernatant was removed. The protein pellets were allowed to air dry. The protein pellets were suspended in a small volume ( 5 µl) of an alkaline solution (containing <0.05N sodium hydroxide, other alkaline solution). After mixing the tube a small volume of (1 µl) tris-hydrochloride (0.5M, other acidic agents) solution was added to each tube to adjust the pH of the protein solution around pH 6-8. The protein suspensions were mixed with (6 µl) Lamelli sample loading buffer, boiled and loaded on a 4-15% gradient SDS-polyacrylamine gels, along side the control sample. After electrophoresis the protein bands were developed using Coomassie dye. Precipitation yield was determined by comparing the color intensity of various protein bands with the control sample ran along side the test samples.

Figure 7:
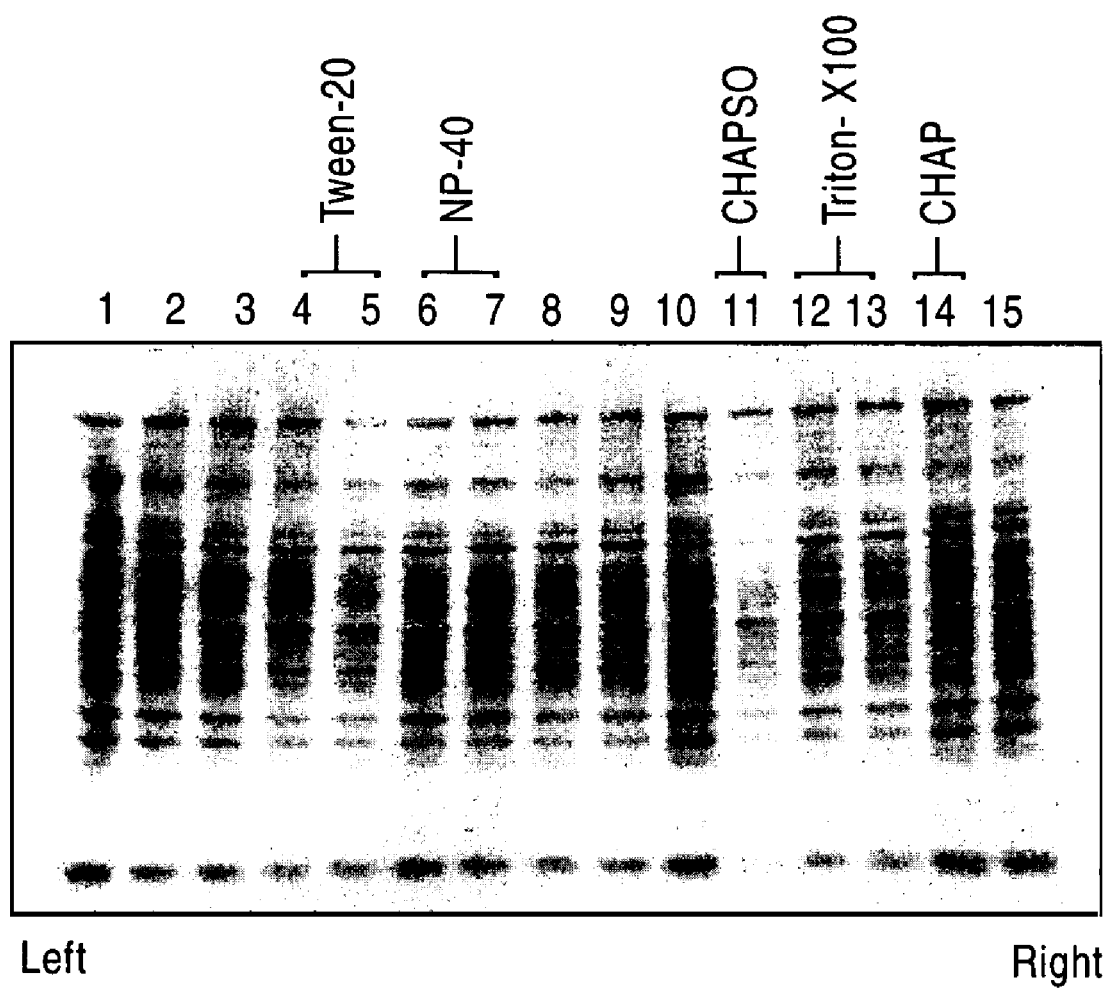
FIG. 7—SDS-gel electrophoresis of protein samples precipitated with protein precipitation agent containing TCA and sodium chloride. The samples were loaded on the gels in the following order (from left to right) lane-1 control sample, lane 2-3 thiodiglycol, lane 4-5 Tween-20, lane 6-7 NP-40, lane 8-9 Brij-35, lane 10 SDS, lane 11 CHAPSO, 12-13 Triton-X100, lane 14 CHAP and lane 15 control.

The FIG. 7 shows the results. The samples were loaded on the gels in the following order (from left to right) lane-1 control sample, lane 2-3 thiodiglycol, lane 4-5 Tween-20, lane 6-7 NP-40, lane 8-9 Brij-35, lane 10 SDS, lane 11 CHAPSO, 12-13 Triton-X100, lane 14 CHAP and lane 15 control. The electrophoresis results shows (after a comparison of several typical runs) that, with exception of SDS and de-oxycholate treated protein samples, most protein samples containing detergent showed batch to batch variation in protein precipitation yield. The protein precipitation yield depended on the techniques used for harvesting the precipitated protein. There were occasions when the precipitation yield of duplicate samples varied between 100% to 50%. Protein samples containing SDS invariably showed substantially 100% yield in multiple tests.

These experiment establishes that protein solutions contain SDS detergent consistently show 100% precipitation yield where as protein solutions containing other types of detergents show batch to batch variation.

This finding should not be confused with the finding of the experiment-3 in which protein solution containing a wide variety of detergents in protein assay format showed linear response of nearly identical slope. A protein assay format, consisting of multiple points tends of mask the variation of individual points within the standard deviation of the plot.

By contrast, in electrophoresis analysis each sample point is examined separately revealing even a small difference.

Example 10

Electrophoretic analysis of protein treated with a protein-precipitation agent containing a precipitate forming agent.

The experiment of the Example-9 was repeated. Except, after treating the protein solution with a protein-precipitation agent (containing TCA and salt), an aliquot of precipitate-forming agent (0.3 ml, 0.1% sodium deoxycholate) was added into the reaction tube and mixed. The rest of the procedure remained the same as described in the Example 9.

Figure 8:
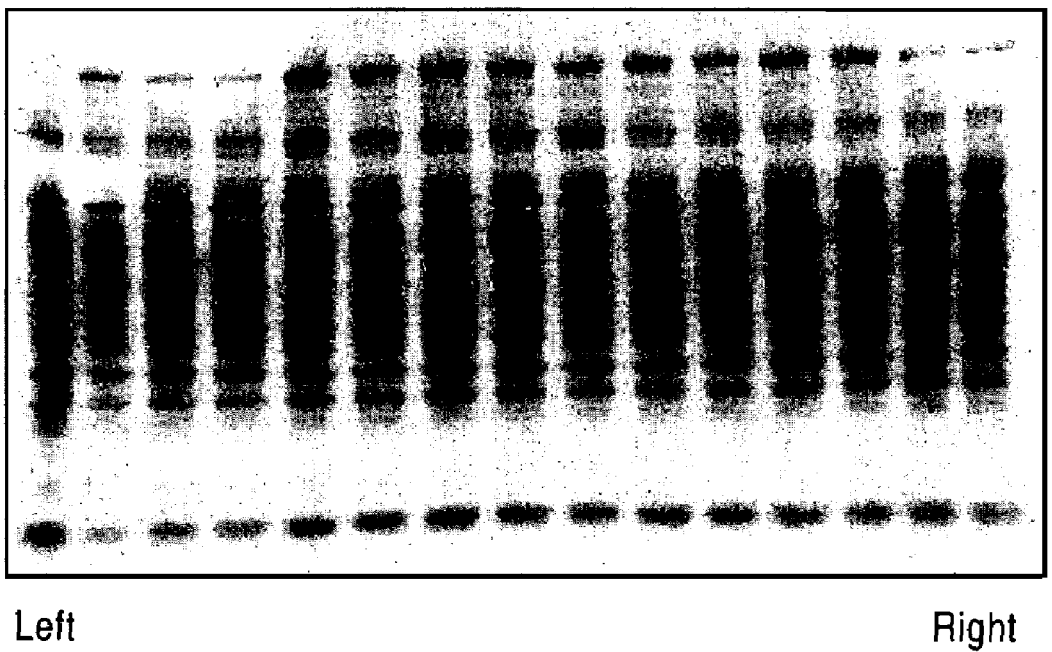
FIG. 8—SDS-gel electrophoresis of protein samples precipitated with precipitation agent containing TCA, sodium chloride, and a precipitate-forming agent. The test samples were loaded on the gels in the following order (from left to right) lane-1 control sample, lane 2 thiodiglycol, lane 3 Tween-20, lane 4 Brij, lane 5 SDS, lane 6 NP-40, lane 7 CHAPSO, lane 8 Triton-X100, lane 9 CHAPS, lane 10 Isotridecylpoly (ethylene-glycolether)$_n$, lane 11 Thesit, lane 12 MEGA-8, lane 13 N-dodecyl-β-D-maltoside, lane 14 N-dedecyl-N-N-demethhyl-3-ammonio-1-propane sulfonate, lane 15 control.

The FIG. 8 shows the results. The test samples were loaded on the gels in the following order (from left to right) lane-1 control sample, lane 2 thiodiglycol, lane 3 Tween-20, lane 4 Brij, lane 5 SDS, lane 6 NP-40, lane 7 CHAPSO, lane 8 Triton-X100, lane 9 CHAPS, lane 10 Isotridecylpoly (ethylene-glycolether)$_n$, lane 11 Thesit, lane 12 MEGA-8, lane 13 N-dodecyl-β-D-maltoside, lane 14 N-dedecyl-N-N-demethhyl-3-ammonio-1-propane sulfonate, lane 15 control. The results showed that when a precipitate-forming agent is added into the mixture of protein and acidic agent, the precipitation yield of protein solutions containing detergents invariably improved to 100% and eliminated the batch-to-batch variations observed in Example 9. This experiment establishes that addition of precipitate-forming agent in protein-precipitation agent improves the precipitation yield of protein solution containing detergents.

Most of the experiments (Examples 2-13) in this invention have also been tested using the protein-precipitation agent containing TCA, 4M sodium chloride, and sodium deoxycholate as a precipitate-forming agent (as detailed in the parent of this application) and have produced identical results.

Example 11

Precipitation of Dilute Protein Solution with Acetone

Aliquots of 2-8 μl from a mouse liver homogenate protein solution (1.18 mg protein/ml) were transferred to a series of microfuge tubes. 100 μl of water was added to each tube and mixed, lowering the final protein concentration to nanogram level. 1 ml acetone (pre-chilled at −20° C.) was added into each tubes and incubated for 1 h-20 h at −20° C. At the end of incubation, tubes were centrifuged and supernatant removed. The pellets were collected and analyzer for protein precipitation yield.

The precipitated protein pellets were analyzed by SDS-gel electrophoresis (as described above) and compared with a control sample (sample not treated with acetone) loaded along side on the same gel. SDS-gel electrophoresis profile of the samples precipitated with acetone revealed that acetone-precipitated sample had several protein bands missing from the electrophoresis patterns and some of those bands that appeared in the acetone-precipitated samples had recovery lower than 100%. It was established that acetone did not qualitatively precipitate all types of protein in mouse liver homogenate. The recovery of missing protein bands did not improved by prolonging the incubation period in acetone solution up to 20 hours.

Example 12

Removal of Detergents and Other Non-protein Agents from Protein Solution:

Most detergents co-precipitate with protein when treated with an acidic agent of the instant invention. The experiments of the Example 10 was repeated, the protein precipitates were collected and chilled (−20 C) acetone (1 ml) was added to each tube. After introducing acetone into the tubes the protein pellet were washed by vortexing the tubes for 1-2 minutes. The pellets were collected by centrifugation and suspended in a buffer solution or water and analyzed for the recovery of protein and the removal of detergents. It was discovered that when the protein pellet is washed with acetone it substantially removed most detergents, acids, and salts from the pellet. The method of present invention has been successfully used in removal of a wide variety of other types of detergents, lipids, natural products.

Example 13

Figure 9:
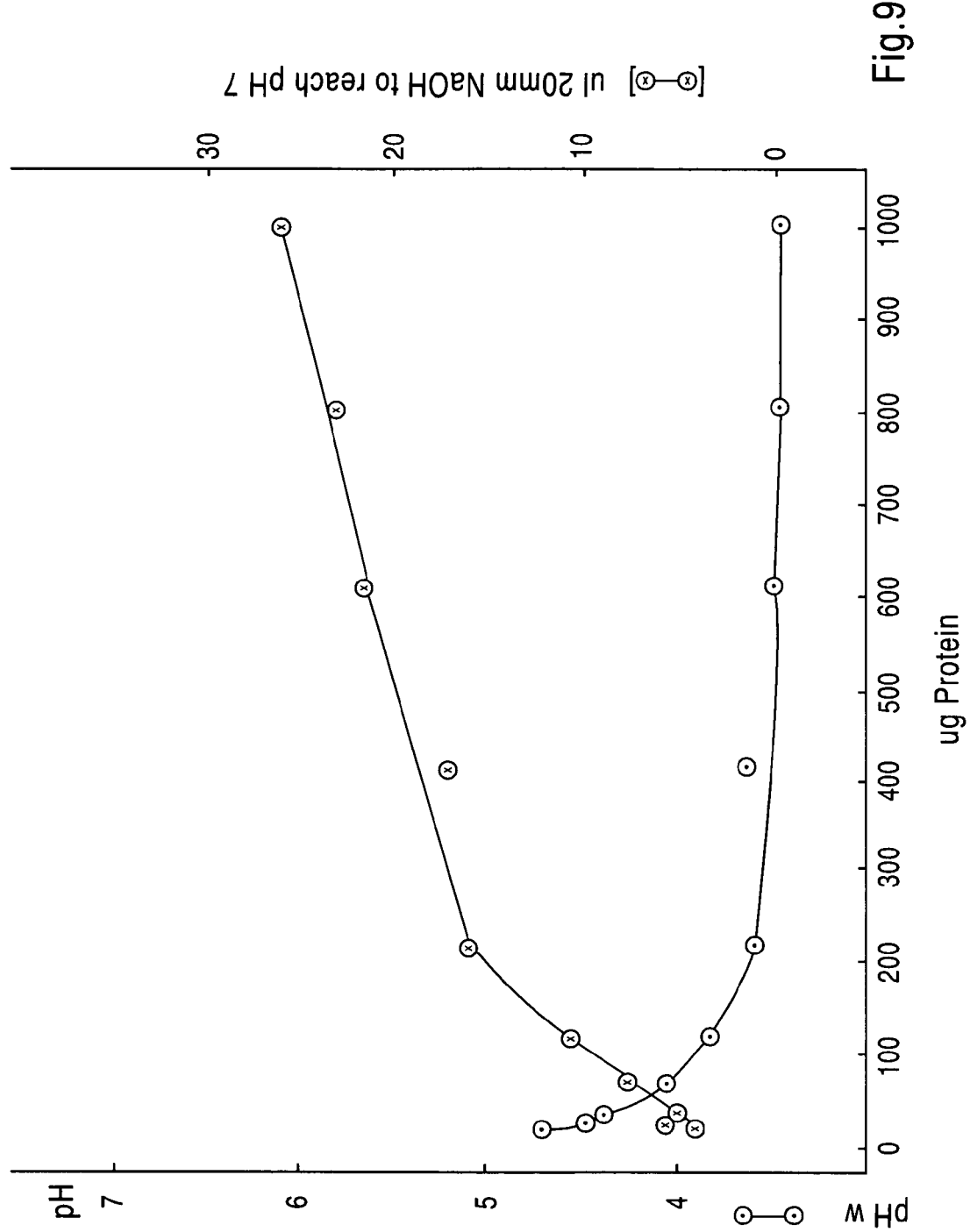
FIG. 9: shows titration of precipitated protein pellets (0-1000 μg) with 20 mM NaOH. NaOH was introduced into the precipitate suspension (1-2 μl at a time ) until the suspension pH eached approximately pH 7.00.

Acid retention by protein pellet was investigated. Mouse liver ground in 2% SDS & 60 mM Tris, pH 7.00 was used as test sample lysate. The lysate containing 0-1000 μg protein was treated as described in the Examples—9 & 10. Briefly, the lysate was first treated with the protein-precipitation agent (0.3 ml) containing 10% TCA and sodium chloride (4M) followed by the addition of a precipitate-forming agent (0.3 ml, 0.1% sodium deoxicholate). After the addition of the precipitate-forming agent (0.3 ml of 0.1% sodium deoxicholate) the suspension was centrifuge at 10-15,000×g for 5-10 minutes. The supernatant was removed and discarded. Any remaining supernatant in the tube was removed by a second brief 10-30 second centrifugation, placing the centrifuge tube in the centrifuge in the same orientation as the previous centrifugation (preferably, placing the cap-hinge out ward) which allowed the protein pellet to remained glued to the same side of the tube minimizing the protein loss. The residual supernatant collected at the bottom of the tube after the second centrifugation was removed using a pipettor (a tipped suction device). The pellet was suspended in a small volume of aqueous medium water (50-100 μl or a volume approximately equal to the size of the protein pellet) and then treated with 5-50 volumes of acetone, as described in Example-9. In some experiments, water and organic solvent was first mixed (mixture of aqueous-organic solvent) and then added to the pellets. Alternatively, the protein precipitate is suspended in a mixture of water(aqueous)-organic solver (acetone). The protein precipitate may be further suspended in organic solvent or the mixture of water-organic solvent The pellet suspension was centrifuge and the protein pellet was collected. After collecting the pellets, the pellet was dried and an aliquot (1 ml) of de-ionized water was added into each tube and vortex for 30 seconds to fully suspend the protein pellets. pH of the solution containing protein pellet suspended in the water was recorded. After recording the pH, the protein pellet suspension was titrated with 20 mM NaOH solution. The 20 mM NaOH, 1-2 μl at a time, was added into the suspension until the suspension pH reached approximately pH 7.00. The pH of the protein pellet suspension and titration with the NaOH are recorded in Table-1 and FIG. 9 show titration.

It was discovered that even after through washing with acetone, the protein pellets retained acid. The amount of acid retained in the pellets were proportion to the amount of total protein content of the pellet. On average each 1 μg protein pellet required >0.01 μg of NaOH to neutralize the acid present in the pellet, i.e. each 1 μg protein pellet retained >0.25 nM acid.

It was also discovered that when the second centrifugation of the pellet (to remove the residual supernatant) was omitted from the method, the residual acid content of protein pellets were much higher and not consistent from tube to tube. Suspending the pellet in aqueous medium water washing the pellet twice with acetone lower of the residual acid content of the protein pellets.

TABLE 1

| Protein (µg) | pH | Volume (µl) of 20 mM NaOH added to reach ~pH 7.00 |
|---|---|---|
| 0 | 4.71 | 4 µl to pH 7.06 |
| 7 µg | 4.46 | 6 µl to pH 7.31 |
| 15 µg | 4.40 | 5 µl to pH 7.36 |
| 50 µg | 4.06 | 8 µl to pH 7.26 |
| 100 µg | 3.84 | 11 µl to pH 7.25 |
| 200 µg | 3.60 | 16 µl to pH 7.08 |
| 400 µg | 3.64 | 27 µl to pH 7.13 |
| 600 µg | 3.5 | 22 µl to pH 7.28 |
| 800 µg | 3.47 | 23 µl to pH 7.06 |
| 1000 µl | 3.46 | 26 µl to pH 7.06 |

Example 14

Affect of pH on the solubility of protein pellet was investigated. Mouse liver ground in 2% SDS & 60 mM Tris, pH 7.00 was used as test sample lysate. Lysate containing (1000 µg) protein was treated as described in the Example-13. The (1000 µg) protein pellets in individual tubes were suspended in 0.1 ml to 0.5 ml solubilization buffer containing 8M urea, 4% NP-40, 0.2% Ampholyte-3/10 and 5 mM Tris, pH 8.38. Each tube was vortex periodically and the protein pellets were allowed to hydrate and solubilize at room temperature. pH of each suspension was determined and recorded. (Table-2).

It was discovered that the pH of each tube got lower (acidic) as the volume of the solubilization buffer added to hydrate the protein pellets decreased. The protein pellets containing 0.5 ml and 0.25 ml solubilzation buffers (pH 7.37 and pH 6.62, respectively) fully solubilized into a clear solution within 30 minutes. On the other hand, the protein pellets containing 0.167 ml, 0.125 ml and 0.1 ml buffer with pH 6.02, pH 5.58 and pH 5.28 respectively did not completely solubilized (solution not clear) even after several hours at room temperature (Table-2).

TABLE 2

| Volume of Pellet Solubilizing Buffer Added (ml) | Protein Concentration (mg/ml) | Protein Solution pH | Protein Solubility in 30–60 minutes |
|---|---|---|---|
| 0.5 ml | 2 mg/ml | 7.37 | Clear solution |
| 0.250 ml | 4 mg/ml | 6.62 | Solution not clear |
| 0.167 ml | 6 mg/ml | 6.02 | Solution not clear |
| 0.125 ml | 8 mg/ml | 5.58 | Solution not clear |
| 0.1 ml | 10 mg/ml | 5.28 | Solution not clear |

It was concluded that as the volume of the solubilization buffer decreased the pH of the solution decreased (become more acidic) and consequently the solubility of the protein pellet got lower (reduced). It must also be noted that the solubilization buffer used herein contained 5 mM tris and ampholyte which helped to neutralized the acid retained within the protein pellet. In separate experiments, the amount of Tris in the solubilization buffer was increased to 10 mM, for the given volume of the solubilization buffer, the suspension resulted in even greater nuetralization of the acid retained in the pellet. The protein pellets containing 0.167 ml, 0.125 ml and 0.1 ml solubilization buffer gave pH 6.7, pH 6.13 and pH 5.75. Thus by increasing the acid neutralizing agent in the solubilization buffer it was possible to increase the capacity to neutralize the acid in the pellet and thus shift the pH of the suspension in favor of greater solubility of the protein in the pellet and achieve desired protein solubility. In a series of experiment it was possible to achieve protein solubility of high concentration (>10 mg protein/ml). The acid neutralizing capacity of the solubilization buffer was achieved by increasing the amount of Trisbase or sodium hydroxide in the solubilization buffer. In a separate experiment, additional amount of trisbase was added to shift the pH of the suspension and achieve desired protein solubility.

In separate experiments, a pH indicator dye (bromphenol blue was added) was added which allowed monitoring of pH of the protein pellet suspension.

Example 15

Affect of grinding on the protein pallet solubility was investigated. In a repeat of the Experiment-14. Tubes contain (1000 µg) protein pellet were suspended in 0.167 ml solubilization buffer ( as described in Example 14) which gave the protein pellet suspension pH 6.00. The tubes were incubated at room temperature for 30-40 minutes. Solubilization of the protein pellets were assisted by mixing the content of the tubes either by vortexing, using a pipettor to suspend and mix the pellet, sonication, or a pestle to grind the pellet. A control sample, without any agitation, was also prepared in which buffer was placed on the pellet the tube was allowed to incubate without any agitation. It was discovered that rapid solubilization of the pellet was achieved (within 30 minutes) when the pellets were mechanically ground with a grinding pestles. Sonication was also helpful in solubilizing the pellet within 30 minutes. Vortexer was least effective. Use of a pepetting tools (i.e. plumping buffer up and down through the pipetor tip) was also not very effective. The control sample without agitation or mixing was not successful in solubilization of the pellet within 30 minutes or even in longer incubation.

Example 16

2D Gel Analysis were performed to investigate the effectiveness of the invention for protein precipitation.

Figure 10A:
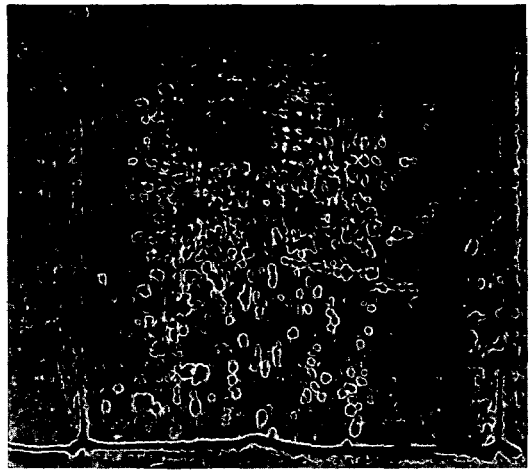
FIG. 10: shows 2D gel maps (A) crude cell lysate, (B) crude cell lysate solubilized in 2% SDS and precipitated according the present invention and re-hydrate for 2D gel analysis, and (C) crude cell lysate precipitated either with TCA, acetone or TCA/Aceton. The precipitate was re-hydrated for 2D analysis.
Figure 10B:

Fully grown cell suspension was lysed by freeze and thaw in deionized water. The crude lysate was was mixed with IEF buffer and 100 µg protein was analyzed by IEF-2D dimension gel analysis (2D gles) (FIG. 10A). Another 100 µg crude extract solubilized in 2% SDS in 60 mM Tris, pH 7.00 was treated as described in the Example-9-13 (i.e. protein solution subjected to precipitation according to the invention followed by rehydration) and analyzed by IEF/2D electrophoresis (FIG. 10B).

Comparing the 2D maps, it was discovered that the sample treated according to the method of instant invention allowed precipitation and quantitative recovery of the proteins and produced 2D maps (FIG. 10B) substantially identical to the 2D map of the untreated crude extract (FIG. 10A). In a series of similar experiments, lysate prepared in the presence of other types of detergents (non-ionic Triton-X100, CHAPS etc.) resulted in similar results, i.e. precipitation and re-hydration of the protein was substantially quantitative (identical to the control).

Figure 10C:
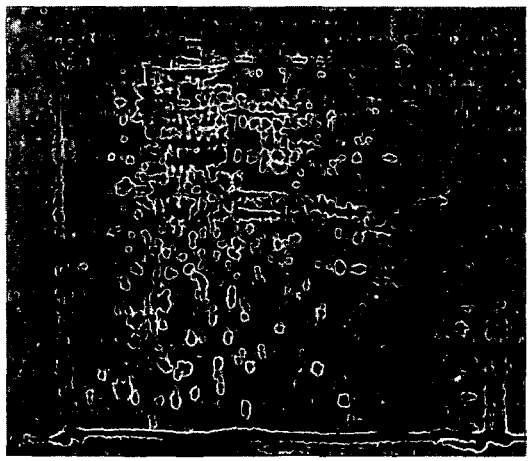

In yet another experiments 100 μg crude extract was treated with TCA, acetone, and a mixture of TAC/acetone and analyzed by IEF-2D. For acetone and TAC/acetone precipitation, the suspension was incubation for 3 h at −20 C, the protein pellet was recovered and analyzed by IEF-2D dimension gel analysis (2D gles). It was discovered, as compared to the control (no treatment) 2D map (FIG. 10A), a fairly large number of proteins (spots) were missing from the 2D maps of the protein treated with TAC, acetone and TCA/acetone (FIG. 10C).

What is claimed is:

1. A method of preparation of protein sample solution for analysis, wherein the protein sample solution contains one or more of non-protein agents selected from a group consisting of an anionic detergent, a cationic detergent, a non-ionic detergent, a zwitterionic detergent, a sulfobutane, a lipid, a polysaccharide, a polyphenol, a tannin, an alkaloid, a pigment, a reducing agent, a protein denaturant, an amine, HEPES, a TRIS buffer, and a salt, wherein after the preparation of the protein sample the protein in the sample is quantitatively recovered and is without interference from the non-protein agents originally present in the sample, comprises the following steps:
   (a) treating the protein sample solution with an acidic agent, and one or both agents selected from a group consisting of a salt and a precipitate-forming agent, wherein the treatment of the protein with the precipitate-forming agent follows the treatment of the protein sample solution with the acidic agent;
   (b) centrifuging the protein sample solution of the step (a) at least once to form a tight pellet at the bottom of the tube, remove and discard the supernatant and collect a protein pellet;
   (c) suspending and mixing the protein pellet of the step (b) at least once in at least one medium selected from a group consisting of a mixture of aqueous-organic solvent and an organic solvent;
   (d) centrifuging the protein pellet suspension of the step (c) and collect the protein pellet; and
   (e) suspending the protein pellet of the step (d) in a protein pellet solubilization reagent buffer, wherein the reagent buffer is provided with an acid neutralizing agent in a sufficient amount to substantially neutralize the acid captured in the protein pellet to facilitate a desired protein solubilization.

2. The method of protein precipitation according to claim 1 wherein the protein sample solution contains an ionic detergent sodium dodecyl sulfate.

3. The method of protein precipitation according to claim 2, wherein the salt agent is in a amount effective to precipitate the detergent present in the protein solution.

4. The method of claim 1 wherein the salt is provided in a solution with the acid agent.

5. The method of claim 1 wherein the precipitate-forming agent is a deoxycholate.

6. The method according to claim 1 wherein the precipitate-forming agent is soluble and extractable in the organic solvent.

7. The method according to claim 1 wherein the organic solvent is selected from a group consisting of an acetone and an alcohol.

8. The method of claim 1 further comprises first suspending the protein pellet of the step (b) in an aqueous medium followed by suspension in the organic solvent.

9. The method of claim 1 further comprises mixing a polysaccharide solution with the protein pellet of the step (b).

10. The method according to claim 1 wherein the pellet solubilization reagent buffer is provided with a pH indicator dye.

11. The method of claim 1 further comprises vigorously agitating and/or grinding the protein pellet suspended in the pellet solubilization reagent buffer in the step (e).

12. The method of claim 1 further comprises addition of an acid neutralizing agent into the pellet solubilization buffer to shift the pH of the suspension to favor desired protein solubilization.

13. The method of claim 1 wherein the centrifugation in the step (b) is repeated to remove residual supernatant.

14. The method according to claim 1 wherein the second centrifugation in step (d) is performed by placing the tube in the centrifuge in the sample orientation as before.

15. The method of claim 1 further comprises addition of an acid neutralizing agent to neutralize approximately or greater than 0.25 nM acid per micro-gram protein in the pellet to favor desired protein solubilization.

16. A method of preparation of protein sample solution for analysis, wherein the protein sample solution contains one or more of non-protein agents selected from a group consisting of an anionic detergent, a cationic detergents, a non-ionic detergent, a zwitterionic detergent, a sulfobutane, a lipid, a polysaccharide, a polyphenol, a tannin, an alkaloid, a pigment, a reducing agent, a protein denaturant, an amine, HEPES, a TRIS buffer, and a salt, wherein after the preparation of the protein sample the protein in the sample is quantitatively recovered and is without interference from the non-protein agents originally present in the sample, comprises the following steps:
   (a) treating the protein sample solution with an acidic agent, and one or both agents selected from a group consisting of a salt-and a precipitate-forming agent, wherein the treatment of the protein with the precipitate-forming agent follows the treatment of the protein sample solution with the acidic agent;
   (b) centrifuging the protein sample solution of the step (a) to form a tight pellet at the bottom of the tube, remove and discard the supernatant and repeat the centrifugation to remove the residual supernatant with a tipped device and collect a protein pellet;
   (c) suspending and mixing the protein pellet of the step (b) at least once in at least one medium selected from a group consisting of a mixture of aqueous-organic solvent and an organic solvent;
   (d) centrifuging the protein pellet suspension of step (c) and collect the protein pellet; and
   (e) suspending the protein pellet of the step (d) in a protein pellet solubilization reagent buffer, wherein the reagent buffer is provided with an acid neutralizing agent to neutralize approximately or greater than 0.25 nM acid per micro-gram protein in the pellet to facilitate a desired protein solubilization.

17. The method of claim 16 further comprises mixing a polysaccharide with the protein pellet of the step (b).

18. The method of protein precipitation according to claim 16 wherein the protein sample solution contains an ionic detergent sodium dodecyl sulfate.

19. The method of protein precipitation according to claim 18, wherein the salt agent is in a amount effective to precipitate the detergent present in the protein solution.

20. The method of claim 16 wherein the salt is provided in a solution with the acid agent.

21. The method according to claim 16 wherein the pellet solubilization reagent buffer is provided with a pH indicator dye.

22. The method of claim 16 further comprises vigorously agitating and/or grinding the protein pellet suspended in the pellet solubilization reagent buffer in the step (e).

23. A method of total protein assay, wherein the protein sample contains one or more of non-protein agents selected from a group consisting of an anionic detergent, a cationic detergent, a non-ionic detergent, a zerterionic detergent, a sulfobutane, a lipid, a polysaccharide, a polyphenol, a tannin, an alkaloid, a pigment, a reducing agent, a protein denaturant, an amine, HEPES, a TRIS buffer, and a salt, comprises the following steps:

(a) treating the protein sample solution with an acidic agent, and one or both agents selected from a group consisting of a salt and a precipitate-forming agent, wherein the treatment of the protein with the precipitate-forming agent follows the treatment of the protein sample solution with the acidic agent;

(b) centrifuging the protein sample solution of the step (a) at least once to form a tight pellet at the bottom of the tube, remove and discard the supernatant and collect a protein pellet;

(c) suspending the protein pellet of the step (b) with one or more alkaline reagents of a protein assay to produce a characteristic protein reaction; and (d) comparing the color density of the protein color reaction with the color density of a protein reaction of known protein concentration.

* * * * *